United States Patent
Patel

(10) Patent No.: US 7,442,821 B2
(45) Date of Patent: Oct. 28, 2008

(54) PROCESS FOR PREPARING UNSATURATED IMIDOALKOXYSILANES

(75) Inventor: Ben Patel, Niskayuna, NY (US)

(73) Assignee: Momentive Performance Materials Inc., Wilton, CT (US)

( * ) Notice: Subject to any disclaimer, the term of this patent is extended or adjusted under 35 U.S.C. 154(b) by 390 days.

(21) Appl. No.: 11/287,756

(22) Filed: Nov. 28, 2005

(65) Prior Publication Data

US 2007/0123728 A1    May 31, 2007

(51) Int. Cl.
*C07F 7/10* (2006.01)
(52) U.S. Cl. .................. 556/407; 556/419; 548/548
(58) Field of Classification Search ........... 556/407, 556/419; 548/548
See application file for complete search history.

(56) References Cited

U.S. PATENT DOCUMENTS

| | | | |
|---|---|---|---|
| 3,576,031 A * | 4/1971 | Holub et al. ............. | 556/419 |
| 3,755,354 A | 8/1973 | Holub et al. | |
| 4,122,076 A * | 10/1978 | Jablonski et al. ............. | 528/322 |
| 6,191,286 B1 * | 2/2001 | Gunther et al. ............. | 548/548 |
| 6,222,055 B1 * | 4/2001 | Wolter et al. ................ | 556/413 |
| 6,441,213 B1 * | 8/2002 | Musa et al. ................. | 556/418 |
| 2004/0152905 A1 * | 8/2004 | Guzaev et al. ............. | 548/453 |

FOREIGN PATENT DOCUMENTS

JP        XP002428698        1/1999

* cited by examiner

*Primary Examiner*—Margaret G Moore
(74) *Attorney, Agent, or Firm*—Dominick G. Vicari

(57) ABSTRACT

A process is provided for preparing unsaturated imidoalkoxysilane which comprises imidating substantially water-free Diels-Alder protected unsaturated N-substituted cyclic imide with aminosilane to provide Diels-Alder protected unsaturated imidoalkoxysilane without the use of chemical desiccants. The Diels-Alder protected unsaturated imidoalkoxysilane produced is then deprotected to provide unsaturated imidoalkoxysilane and the Diels-Alder protecting diene is regenerated to the process. A Diels-Alder intermediate is also provided.

27 Claims, No Drawings

PROCESS FOR PREPARING UNSATURATED IMIDOALKOXYSILANES

FIELD OF THE INVENTION

The present invention relates to a process for preparing α,β-unsaturated cyclic imidoalkoxysilanes from anhydride precursors, without the use of a chemical desiccant to scavenge the water produced as a side product.

BACKGROUND OF THE INVENTION

There are different processes for making α,β-unsaturated cyclic imidoalkoxysilanes that are known in the art. These processes are based on the condensation of anhydride precursors with primary aminoalkoxysilanes, and produce water as one of the reaction by-products. Typically, the water produced is scavenged from the reaction using one or more chemical desiccants, for example hexamethyldisilazane (HMDZ) or trimethylsilyl chloride (TMSCI). These chemical desiccants must be used in at least stoichiometeric amounts, which makes these processes economically unfeasible when used to produce α,β-unsaturated cyclic imidoalkoxysilanes on a large commercial scale.

One object of the invention is directed to a process for producing α,β-unsaturated cyclic imidoalkoxysilanes under conditions favorable to allow the removal of water produced by reaction using azeotropic distillation instead of chemical desiccants. In particular this object of the invention is directed to a process for making α,β-unsaturated cyclic imidoalkoxysilanes using a Diels-Alder protection strategy without using chemical desiccants.

Another object of the invention is directed to stable Diels-Alder intermediates that can be used to produce α,β-unsaturated cyclic imidoalkoxysilanes of the present invention.

Still another object of the invention is directed to the process for producing a Diels-Alder unsaturated N-substituted aromatic imide using an aromatic primary amine and an anhydride precursor in a solvent that permits the removal of water using azeotropic distillation instead of a chemical desiccant.

The objects of the present invention overcome the shortcomings of the known processes and are further described below.

SUMMARY OF THE INVENTION

The present invention describes the production of α,β-unsaturated cyclic imidoalkoxysilane compounds without the use of costly chemical desiccants. In particular, the present invention is directed to a process for preparing α,β-unsaturated cyclic imidoalkoxysilane which comprises transimidating a substantially water-free Diels-Alder protected unsaturated N-substituted aromatic imide with at least one aminoalkoxysilane to provide at least one Diels-Alder protected unsaturated cyclic imidoalkoxysilane. The Diels-Alder protected unsaturated cyclic imidoalkoxysilane produced is then deprotected to provide unsaturated imidoalkoxysilane and the Diels-Alder protecting diene is regenerated to the process.

The present invention is also directed to a Diels-Alder intermediate having the general formula:

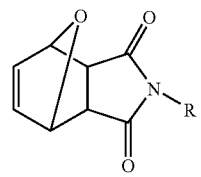

wherein R is a primary aromatic amine, a primary arylamine or a primary heteroarylamine.

One advantage of the inventive process for making the unsaturated imidoalkoxysilane is that the reaction can be carried out without the addition of caustic and costly chemical desiccants. Instead, water produced in the reaction, which must be removed so as not to hydrolyze the alkoxy groups of the silane, is removed using azeotropic distillation. Therefore, the process can be done on a commercial scale more economically than processes that use the chemical desiccants to remove the water produced during the process. An added benefit of the inventive process is that the aromatic primary amine used in the reaction as well as the Diel-Alder diene used to protect the double bond in the starting anhydride are recycled in the reaction making the reaction mechanism even more economically favorable over the reaction mechanisms known in the art.

DETAILED DESCRIPTION OF THE INVENTION

The present invention describes the production of α,β-unsaturated cyclic imidoalkoxysilane compounds without the use of costly chemical desiccants. In particular, the present invention is directed to a process for preparing α,β-unsaturated cyclic imidoalkoxysilane from a cyclic anhydride precursor using an imidation step, a Diels Alder protection step, a transimidation step, and a deprotection step. One mechanism of the present invention is described in the reaction mechanism shown below.

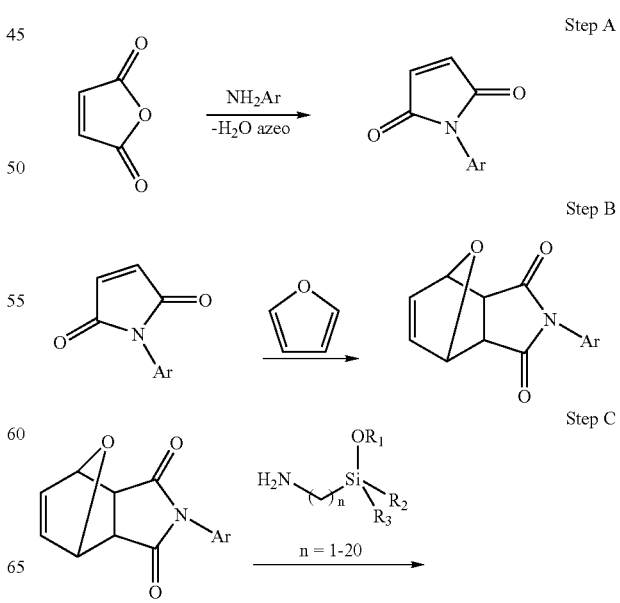

-continued

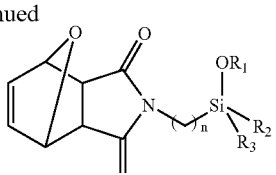

n = 1-20

Step D

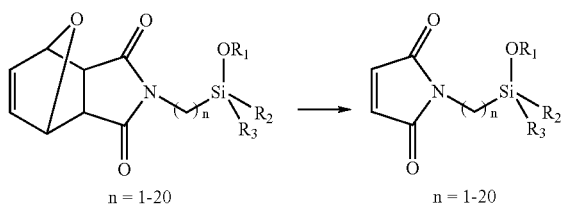

n = 1-20             n = 1-20

The imidation step is carried out in an organic solvent which forms an azeotrope with water, which allows the removal of water from the product mixture via azeotropic distillation. This step eliminates the need for any type of chemical desiccant.

A Diels-Alder reaction (also called the 4+2 cycloaddition reaction) is a well-known technique for the synthesis of six member rings. This reaction involves the 1,4-addition of the double bond of a dienophile to a conjugated diene to generate a six-member ring. In the present invention, the use of a Diels-Alder protection strategy is employed to protect the unsaturation in the aromatic imide product, from nucleophilic reduction, in order to assure that this α,β-unsaturated double bond remains in tact in the final product. The resulting Diels-Alder protected unsaturated N-substituted aromatic cyclic imide can then be reacted with a nucleophile, such as an aminoalkoxysilane, e.g. aminopropyltriethoxysilane, to produce the protected derivative of the desired product, which can then be thermally deprotected.

For the inventive process described herein the diene can include cyclic, heterocyclic and highly substituted materials providing the diene is "psuedo aromatic." These "psuedo aromatic" dienes are further discussed below.

One aspect of the invention is directed to a process which comprises transimidating a substantially water-free Diels-Alder protected unsaturated aromatic N-substituted cyclic imide with at least one aminoalkoxysilane to provide at least one Diels-Alder protected unsaturated cyclic imidoalkoxysilane. The Diels-Alder protected unsaturated aromatic N-substituted cyclic imide can be obtained by the process which comprises imidating an α,β-unsaturated carboxylic acid anhydride with at least one primary aromatic amine to provide at least one unsaturated aromatic N-substituted cyclic imide. The conjugated double bond of the unsaturated aromatic N-substituted imide is then reacted with a psuedo aromatic diene under Diels-Alder reaction conditions so as to protect the double bond from reacting. For example, protecting the conjugated double bond of the unsaturated aromatic N-substituted cyclic imide eliminates the possibility of any Michael or "ene-type" reactions at the double bond by a nucleophile, therefore preserving the double bond in the product upon the completion of the deblocking step.

In another aspect of the invention, the Diels-Alder protected α,β-unsaturated aromatic N-substituted cyclic imide is obtained by the process which comprises protecting the double bond of an α,β-unsaturated cyclic anhydride with a "psuedo aromatic" diene under Diels-Alder reaction conditions to provide Diels-Alder protected unsaturated cyclic anhydride. The Diels-Alder protected unsaturated cyclic anhydride is then imidated with at least one primary aromatic amine to produce at least one Diels-Alder adduct, namely a Diels-Alder protected unsaturated aromatic N-substituted cyclic imide.

Water is produced as part of the transimidating step of the reaction mechanism which can lead to premature hydrolysis of the alkoxysilanes if not removed. Chemical desiccants have conventionally been used in order to remove the water from the reaction mix so as to prevent the water from reacting with other reactants in the mixture to produce unwanted side-products. As stated above, these desiccants are very costly and therefore make the reaction economically challenging when produced on a large commercial scale. The process of the present invention avoids using these costly desiccants by conducting the reaction in solvents that allow the water to be removed using azeotropic distillation. In other words, the N-substituted aromatic cyclic imide of the imidating step is separated from water by azeotropic distillation prior to completing the reaction mechanism of the present invention.

Possible azeotropic solvents that can be used in the reaction include but are not limited to toluene, xylenes, orthodichlorobenzene, or any other relatively high boiling organic solvents that the starting materials of the reaction, namely the unsaturated cyclic anhydride and the primary aromatic amine, are soluble and forms an azeotrope with water. Forming the azeotrope with water allows the water to be removed from the reaction vessel by azeotropic distillation.

As stated above, the diene used in the Diels-Alder reaction must be "pseudo-aromatic", that is the diene must possess aromatic characteristics without actually being aromatic. The term "pseudo aromatic" refers to a conjugated system which is not strictly aromatic, but which is stabilized by means of delocalization of pi-electrons and behaves in a similar manner to aromatic rings. Examples of pseudoaromatic rings include, but are not limited to, furan, thiophene, pyrole, anthracenes, fulvenes, and the like. In the context of the present invention, the term "pseudo-aromatic" diene is meant to include those cyclic dienes in which the atoms of the cyclic structure, both carbon and heteroatoms, possess $Sp^2$-hybridization character so as to allow at least partial delocalization of the conjugated electrons throughout the ring. The significance of using a "psuedo aromatic" diene instead of a typical diene for the blocking step of the Diels-Alder reaction is that the pseudo-aromatic diene can typically undergo reverse Diels-Alder reactions at significantly lower temperatures than typical dienes. In the context of the present invention a relatively low temperature for the removal of the diene moiety is below about 200 degree Celsius. In other words, using an aromatic diene in the Diels-Alder reaction as the protecting group would require that the deprotecting step be carried out at a temperature of above about 200° C., wherein using a psuedo aromatic diene as the protecting group would allow the deprotecting step to occur at a temperature below about 200° C. The lower temperature not only saves energy, but also reduces the production of potential side-products making purification easier.

Possible "pseudo-aromatic" dienes that can be used in the Diels-Alder reaction as the blocking group include but are not limited to the following: furan, substituted furans, including but not limited to 2,3-bishydroxymethyl furan, 3,4-bishydroxymethyl furan, and 2,5-bishydroxymethyl furan, fulvene, substituted fulvenes including but not limited to 6,6-dimethylfulvene, anthracene and substituted anthracenes. The dienes may be monosubstituted or polysubstituted with various functional groups. The functional groups may be selected from the group consisting of alkyl chains ($C_2$-$C_{20}$, methyl, ethyl, iso-propyl, tert-butyl, etc.), OH, SH, halogens, aryl, carboxyl, carbonyl, nitro, carboxyamido, keto, sulfoxide, sulfone, sulfonic acid, phosphoric acid and amino groups, which are bound directly or via alkyl residues.

A Diels-Alder intermediate having the general formula

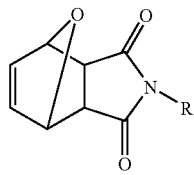

wherein R is a primary aromatic amine, a primary arylamine or a primary heteroarylamine is also part of the present invention. This intermediate can be obtained by the process which comprises imidating an α,β-unsaturated carboxylic acid anhydride with at least one primary aromatic amine to provide at least one unsaturated aromatic N-substituted cyclic imide. The conjugated double bond of the unsaturated aromatic N-substituted imide is then reacted with a psuedo aromatic diene under Diels-Alder reaction conditions so as to protect the double bond from reacting. For example, protecting the conjugated double bond of the unsaturated aromatic N-substituted cyclic imide eliminates the possibility of any Michael or "ene-type" reactions at the double bond by a nucleophile, therefore preserving the double bond in the product upon the completion of the deblocking step.

The Diels-Alder protected unsaturated aromatic N-substituted cyclic imide can then be reacted with a nucleophile such as an aminopropyltrialkoxysilane molecule in the presence of a suitable Lewis acid to produce a Diels-Alder protected unsaturated cyclic imidoalkoxysilane. Other aminoalkoxysilanes can be used providing they have at least one alkoxy group. Examples of appropriate aminoalkoxyosilanes that can be used in transimidating step include but are not limited to aminoalkoxysilanes having the general chemical formula I:

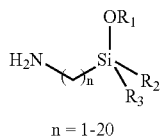

n = 1-20 wherein $R^1$ is an alkylene or cycloalkylene group of from 1 to about 20 carbon atoms or an arylene group of from 6 to about 20 carbon atoms, $R^2$ and $R^3$ each is independently is an alkoxy, an alkyl or cycloalkyl group of from 1 to about 20 carbon atoms or an aryl group of from 6 to about 20 carbon atoms, and n is an integer from about 1 to about 20.

Even more particularly, the aminoalkoxysilane used in the transimidating step can be at least one aminosilane selected from the group consisting of aminomethyl-triethoxy-silane, (3-amino-propyl)triethoxy-silane, (3-amino-propyl)-methyl-diethoxy-silane, (3-amino-propyl)-phenyl-dimethoxy-silane, (4-amino-butyl)triethoxy-silane, (3-amino-2-methyl-propyl)-triethoxy-silane, (4-amino-butyl)-methyl-diethoxy-silane, (3-aminopropoxypropyl)-triethoxy-silane, (3-amino-propoxypropyl)-trimethoxy-silane, (3-amino-propoxypropyl)-methyl-diethoxysilane, (3-amino-propoxypropyl)-ethyl-diethoxy-silane, (p-aminophenyl)-triethoxy-silane, (2-amino-ethylaminomethyl)-(methoxyethoxy)-bis-(1-methylpropylidene aminoxy)-silane and [(.omega.-amino-alkylamino)-alkyl]-trialkoxy-silanes, and, especially, [3-(2-amino-ethylamino)-propyl]-trimethoxysilane, [3-(3-amino-propylamino)-propyl]-triethoxy-silane, [(2-amino-ethylamino)-methyl]-triethoxy-silane and [(6-aminohexylamino)-methyl]-trimethoxy-silane.

As stated above, the transimidating step can be carried out in the presence of a Lewis Acid. An example of a suitable Lewis Acid includes but is not limited to $ZnCl_2$. Other suitable Lewis acids include but are not limited to alkali metal salts and oxides, alkaline earth metal halogen salts and oxides, lanthanide halogen salts and oxides, and any mixtures thereof.

Another aspect of the invention provides for the production of the Diels-Alder protected unsaturated N-substituted cyclic imide, which comprises imidating an unsaturated cyclic anhydride with at least one primary aromatic amine to provide at least one unsaturated aromatic N-substituted cyclic imide. Possible aromatic primary amines include primary arylamines or a primary heteroarylamines. The primary amines must be aromatic and may either be highly substituted or contain no substitutions at all. For example, the aromatic portion of the aromatic primary amine can be substituted with alkyl groups having 1-20 carbons, other aromatic R groups, and/or at least 1 halogen. In particular, the aromatic primary amines used in the present invention may include but are not limited to the following: aniline, ring substituted anilines, 2-amino pyridine, amino naphthalenes, and amino anthracenes.

As stated above, once the protected unsaturated aromatic N-substituted cyclic imide is produced, it is reacted with an aminoalkoxysilane having the general structure I shown above, optionally in the presence of a Lewis acid and optionally with heat to produce an unsaturated cyclic imidoalkoxysilane via a transimidation step. In this transimidation step, the aromatic primary amine is regenerated and can be recycled to the process.

The above reactions may take place in the presence or absence of suitable chemical catalyst. In addition, each of the steps of the reaction can be controlled by heat and or pressure. In particular, the transimidating step may be carried out at a pressure of from about 0.1 atm to about 20 atm and a temperature of from about 25° C. to about 200° C. The deprotecting step of the present invention may be carried out at a pressure of from about 0.1 atm to about 20 atm and a temperature of from about 25° C. to about 200° C.

The following steps illustrate the present invention.

Production of N-Phenylmaleimide from Hot Toluene Solution

A 100 mL round bottom flask was charged with 2.3 grams of maleic anhydride, 50 mL of orthodichlorobenze (o-DCB), and one equivalent of aniline. The flask was connected to a Dean-Stark condenser/trap apparatus, and the resulting solution was heated to reflux. After 60 minutes of refluxing, the water phase was removed from the trap, and the resulting o-DCB solution was recovered. Analysis by standard GC techniques revealed essensially quantitative conversion of the anhydride to N-phenylmaleimide by comparison to a commercially available authentic sample. The N-phenylmaleimide was recovered from the solution at >90% yield by removing the solvent under vacuum and recrystalizing the N-phenylmaleimide from a hot toluene solution.

Production of the Diels-Alder Protected Adduct of Furan and N-Phenylmaleimide

A 250 mL round bottom flask was charged with 10.1 grams of N-phenylmaleimide and 100 mL of toluene. The resulting homogeneous green solution was heated to 90 degree celcius while stirring, and 4.1 grams of furan was added dropwise over a 3 minute period, and the flask was sealed and stirred for 60 minutes. The warm solution was then allowed to cool to room temperature, which caused the precipitation of analytically pure product, in about 70% yield, which was determined by standard HPLC, proton and carbon NMR, and mass spectrometry techniques to be the Diels-Alder protected adduct of furan and N-phenylmaleimide.

Production of the product of the Deils-Alder Adduct of Furan and N-(Propyltriethoxysilane) Maleimide A 50 mL round bottom flask was charged with 20 mL of toluene, 1.6 grams of 3-aminopropyltriethoxysilane, and 1.6 grams of the Diels-Alder protected adduct of furan and N-phenylmaleimide. The colorless suspension was stirred at room temperature over a 12 hr period, during which time the solution become homogenous pale yellow in appearance. Subsequent removal of the solvent under vacuum, lead to the isolation of a dark oily material, which was then quantitatively transferred to a 100 mL round bottom flask charged with 50 mL of dry orthodilchlorbenzene (o-DCB) and heated to about 140 degrees celcius for about 5 hours. The solution was then cooled to room temperature and the o-DCB solvent was removed under vacuum. Subsequent analysis by standard GC, HPLC, and proton and carbon NMR techniques showed the product to be Diels-Alder adduct of furan and N-(propyltriethoxysilane)maleimide in effectively quantitative yield.

Production of (Propyltriethoxysilane) Maleimide

A 50 mL round bottom flask was charged with 1 gram of the Diels-Alder adduct of furan and N-(propyltriethoxysilane)maleimide and 10 mL of orthodichlorobenzene. The resulting homogeneous solution was heated to 150 degree celcius for 1 hour, and then cooled to room temperature. Subsequent removal of all volatiles, including solvent, under vacuum resulted in a dark oil which was determined by standard GC, HPLC, proton and carbon NMR, and mass spectrometry analyses to be N-(propyltriethoxysilane)maleimide in effectively quantitative yield.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A process for preparing unsaturated cyclic imidoalkoxysilane, which comprises:
    i) transimidating substantially water-free Diels-Alder protected unsaturated aromatic N-substituted cyclic imide with at least one aminoalkoxysilane to provide at least one Diels-Alder protected unsaturated cyclic imidoalkoxysilane.

2. The process of claim 1 further comprising:
    ii) deprotecting the protected cyclic imidoalkoxysilane to provide an αβ-unsaturated cyclic imidoalkoxysilane.

3. The process of claim 1 wherein the Diels-Alder protected unsaturated aromatic N-substituted cyclic imide is obtained by a process which comprises imidating a cyclic unsaturated anhydride with at least one primary aromatic amine to provide at least one unsaturated aromatic N-substituted cyclic imide and protecting the double bond of the unsaturated N-substituted cyclic imide with at least one diene under Diels-Alder reaction conditions to provide at least one Diels-Alder protected unsaturated aromatic N-substituted cyclic imide.

4. The process of claim 1 wherein the Diels-Alder protected unsaturated aromatic N-substituted cyclic imide is obtained by a process which comprises protecting the double bond of unsaturated cyclic anhydride with at least one diene under Diels-Alder reaction conditions to provide at least one Diels-Alder protected unsaturated cyclic anhydride and imidating the Diels-Alder protected anhydride with at least one primary aromatic amine, to produce Diels-Alder protected unsaturated aromatic N-substituted cyclic imide.

5. The process of claim 2 wherein the Diels-Alder protected unsaturated aromatic N-substituted cyclic imide of transimidating step (i) is separated from water prior to conducting step (ii).

6. The process of claim 2 wherein the Diels-Alder protected unsaturated aromatic N-substituted cyclic imide of transimidating step (i) is separated from water by azeotropic distillation prior to conducting step (ii).

7. The process of claim 2 wherein the regenerated diene of step (ii) is recycled to process.

8. The process of claim 3 wherein the primary aromatic amine is a primary arylamine or a primary heteroarylamine.

9. The process of claim 8 wherein the primary aromatic amine is at least one member selected from the group consisting of aniline, ring substituted anilines, 2-amino pyridine, amino naphthalenes, and amino anthracenes.

10. The process of claim 3 wherein the diene is at least one member selected from the group consisting of furan, substituted furans, fulvene, substituted fulvenes, anthracene and substituted anthracenes.

11. The process of claim 3 wherein the regenerated diene of step (ii) is at least one member selected from the group consisting furan, substituted furans, fulvene, substituted fulvenes, anthracene and substituted anthracenes, and the primary aromatic amine is selected from the group selected from a primary arylamine, a primary heteroarylamine, aniline, ring substituted anilines, 2-amino pyridine, amino naphthalenes, and amino anthracenes.

12. The process of claim 11 wherein the regenerated diene of step (ii) comprises substitution groups selected from the group consisting of alkyl chains having about 2 to about 20 carbons, methyl, ethyl, iso-propyl, tert-butyl, OH, SH, halogens, aryl, carboxyl, carbonyl, nitro, carboxyamido, keto, sulfoxide, sulfone, sulfonic acid, phosphoric acid and amino groups.

13. The process of claim 1 wherein transimidation is conducted employing at least one step (i) aminoalkoxy silane having the general formula:

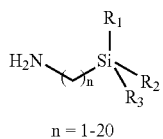

n = 1-20 wherein $R^1$ is an alkoxy, alkylene or cycloalkylene group of from 1 to about 20 carbon atoms or an arylene group of from 6 to about 20 carbon atoms, $R^2$ and $R^3$ each is independently is an alkoxy, alkyl or cycloalkyl group of from 1 to about 20 carbon atoms or an aryl group of from 6 to about 20 carbon atoms, and n is an integer from about 1 to about 20.

14. The process of claim 13 wherein $R^1$ is an alkoxy group of from 1 to 4 carbon atoms, and n is 3.

15. The process of claim 1 wherein transimidating step (i) is conducted employing at least one aminoalkoxysilane selected from the group consisting of aminomethyl-triethoxy-silane, (3-amino-propyl)triethoxy-silane, (3-amino-propyl)-methyl-diethoxy-silane, (3-amino-propyl)-phenyl-dimethoxy-silane, (4-amino-butyl)triethoxy-silane, (3-amino-2-methyl-propyl)-triethoxy-silane, (4-amino-butyl)-methyl-diethoxy-silane, (3-aminopropoxypropyl)-triethoxy-silane, (3-amino-propoxypropyl)-trimethoxy-silane, (3-amino-propoxypropyl)-methyl-diethoxysilane, (3-amino-propoxypropyl)-ethyl-diethoxy-silane, (p-aminophenyl)-triethoxy-silane, (2-amino-ethylaminomethyl)-(methoxy-ethoxy)-bis-(1-methylpropylidene aminoxy)-silane and [(.omega.-amino-alkylamino)-alkyl]-trialkoxy-silanes, and, especially, [3-(2-amino-ethylamino)-propyl]-trimethoxysilane, [3-(3-amino-propylamino)-propyl]-triethoxy-silane, [(2-amino-ethylamino)-methyl]-triethoxy-silane and [(6-aminohexylamino)-methyl]-trimethoxy-silane.

16. The process of claim 1, wherein transimidating step (i) is carried out in the presence of solvent.

17. The process of claim 16 wherein the solvent forms an azeotrope with water.

18. The process of claim 17 wherein the solvent is at least one member selected from the group consisting of toluene, xylenes, orthodichlorobenzene, and mixture thereof.

19. The process of claim 13 wherein transimidating step (i) is carried out in the presence of catalyst.

20. The process of claim 19 wherein the catalyst is a Lewis acid.

21. The process of claim 13 wherein imidating step (a) is carried out at a pressure of from about 0.1 atm to about 20 atm and a temperature of from about 25° C. to about 200° C.

22. The process of claim 2 wherein the deprotecting step (ii) is carried out in the presence of solvent.

23. The process of claim 22 wherein solvent is a Lewis Acid.

24. The process of claim 22 wherein deprotecting step (ii) is carried out in the presence of catalyst.

25. The process of claim 24 wherein the catalyst is a Lewis acid.

26. The process of claim 22 wherein deprotecting step (ii) is carried out at a pressure of from about 0.1 atm to about 20 atm and a temperature of from about 25° C. to about 200° C.

27. The process of claim 4 wherein the protecting step is carried out in an organic solvent at a temperature above about 60° Celsius and below the boiling point of the organic solvent.

* * * * *